(12) United States Patent
Asada et al.

(10) Patent No.: US 11,191,943 B1
(45) Date of Patent: Dec. 7, 2021

(54) TWO-WAY PRESSURE RELIEF VALVE FOR BLOOD RESERVOIR

(71) Applicant: TERUMO CARDIOVASCULAR SYSTEMS CORPORATION, Ann Arbor, MI (US)

(72) Inventors: Takehiko Asada, Kanagawa (JP); Ryan Clingman, Newark, DE (US); Stephen Koellhoffer, Lincoln University, PA (US); Luke Powers, Wilmington, DE (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 0 days.

(21) Appl. No.: 17/092,656

(22) Filed: Nov. 9, 2020

Related U.S. Application Data

(63) Continuation-in-part of application No. 16/891,173, filed on Jun. 3, 2020.

(51) Int. Cl.
*A61M 39/24* (2006.01)
*F16K 17/194* (2006.01)
*F16K 17/196* (2006.01)

(52) U.S. Cl.
CPC ........... *A61M 39/24* (2013.01); *F16K 17/194* (2013.01); *A61M 2039/2493* (2013.01);
(Continued)

(58) Field of Classification Search
CPC .... F16K 15/04; F16K 15/1401; F16K 15/148; F16K 17/19; F16K 17/194; A61M 39/24;
(Continued)

(56) References Cited

U.S. PATENT DOCUMENTS

| 1,637,076 | A | * | 7/1927 | Heil | .................. F16K 17/194 137/43 |
| 1,724,878 | A | * | 8/1929 | Jensen | ................. F16K 17/36 137/43 |

(Continued)

FOREIGN PATENT DOCUMENTS

| EP | 0617627 B1 | ‡ | 5/1996 | .......... A61M 1/3627 |
| EP | 0617627 B1 | | 5/1996 | |

(Continued)

*Primary Examiner* — William M McCalister
(74) *Attorney, Agent, or Firm* — Darryl Newell; MacMillan, Sobanski & Todd, LLC

(57) ABSTRACT

A pressure relief valve for a reservoir has a housing body forming first and second subchambers in fluid communication. A first opening in a bottom surface of the housing body forms a first valve seat. At least one second opening in the bottom surface forms a second valve seat along an outer perimeter. A diaphragm member is biased against the second valve seat and is configured to deflect off of the second valve seat under a negative pressure. A sealing ball is gravitationally biased against the first valve seat and raises off the first valve seat in response to a positive pressure. A cover sheet on an upper surface of the housing body partially encloses the chamber and traps the sealing ball in the first subchamber. The cover sheet includes an aperture aligned with the second subchamber providing an ambient pressure port coupled to ambient atmosphere.

20 Claims, 11 Drawing Sheets

(52) U.S. Cl.
CPC ....... *F16K 17/196* (2013.01); *Y10T 137/7779* (2015.04); *Y10T 137/7842* (2015.04)

(58) Field of Classification Search
CPC ...... A61M 2039/2493; Y10T 137/7779; Y10T 137/7842
USPC .......................................... 137/493.8, 512.3
See application file for complete search history.

(56) References Cited

U.S. PATENT DOCUMENTS

| | | | | |
|---|---|---|---|---|
| 1,944,249 | A * | 1/1934 | Lencke | F16T 1/12 137/512.3 |
| 2,840,105 | A * | 6/1958 | Routledge | F16K 17/19 137/493 |
| 3,587,790 | A * | 6/1971 | Schultze | F16F 9/34 188/281 |
| 3,661,174 | A * | 5/1972 | Cripe | F16K 15/148 137/512.3 |
| 3,913,601 | A * | 10/1975 | Hanson | F16K 17/36 137/39 |
| 4,210,173 | A * | 7/1980 | Choksi | A61M 5/1424 137/512.3 |
| 4,351,350 | A * | 9/1982 | Crute | F16K 17/36 137/39 |
| 4,457,325 | A * | 7/1984 | Green | F16K 17/196 137/39 |
| 4,508,131 | A * | 4/1985 | DeFrees | B60K 15/0406 137/43 |
| 4,671,786 | A * | 6/1987 | Krug | F16K 17/19 604/118 |
| 4,702,268 | A * | 10/1987 | Ambruster | F16K 17/366 137/202 |
| 4,781,686 | A * | 11/1988 | Erickson | A61M 1/3639 137/540 |
| 4,872,474 | A * | 10/1989 | Middleton | A47J 37/1233 137/493.8 |
| 5,035,729 | A * | 7/1991 | Hodgkins | F16K 24/046 96/163 |
| 5,115,830 | A * | 5/1992 | Harde | B60K 15/03519 137/202 |
| 5,158,533 | A | 10/1992 | Strauss et al. | |
| 5,190,067 | A * | 3/1993 | Paradis | A61M 39/04 137/1 |
| 5,325,882 | A * | 7/1994 | Forsythe | B60K 15/03519 137/43 |
| 5,480,054 | A * | 1/1996 | Midden | A47J 41/0005 220/202 |
| 5,499,655 | A * | 3/1996 | Hung | B66F 3/42 137/512.3 |
| 5,707,356 | A * | 1/1998 | Paul | A61M 1/742 604/119 |
| 5,762,093 | A * | 6/1998 | Whitley, II | B60K 15/03519 137/199 |
| 6,017,493 | A ‡ | 1/2000 | Cambron | A61M 1/36 422/44 |
| 7,104,277 | B2 * | 9/2006 | Hernandez | F16K 17/194 137/493.1 |
| 7,243,676 | B2 | 7/2007 | Bailey | |
| 9,435,450 | B2 * | 9/2016 | Muennich | F16K 17/196 |
| 9,657,468 | B1 * | 5/2017 | Di Monte, Sr. | F16K 15/048 |
| 9,902,556 | B2 | 2/2018 | Talon et al. | |
| 9,974,942 | B2 | 5/2018 | Beiriger | |
| 10,179,343 | B2 | 1/2019 | Compton et al. | |
| 2009/0320936 | A1 * | 12/2009 | Brunner | E03C 1/1225 137/533.11 |
| 2014/0260354 | A1 * | 9/2014 | Lundberg | F25B 45/00 62/77 |
| 2018/0236216 | A1 | 8/2018 | Beiriger | |

FOREIGN PATENT DOCUMENTS

| | | | |
|---|---|---|---|
| EP | 0766974 A2 ‡ | 9/1997 | ......... A61M 1/3639 |
| EP | 0766974 A2 | 9/1997 | |

\* cited by examiner
‡ imported from a related application

TWO-WAY PRESSURE RELIEF VALVE FOR BLOOD RESERVOIR

CROSS REFERENCE TO RELATED APPLICATIONS

This application is a continuation-in-part of co-pending U.S. application Ser. No. 16/891,173, filed Jun. 3, 2020, which is incorporated herein by reference in its entirety.

STATEMENT REGARDING FEDERALLY SPONSORED RESEARCH

Not Applicable.

BACKGROUND OF THE INVENTION

The present invention relates in general to medical fluid reservoirs such as a blood reservoir of a perfusion system, and, more specifically, to a pressure relief valve for a medical fluid reservoir.

Fluid systems commonly include components such as tubing, pumps, reservoirs, heat exchangers, sensors, filters, valves, and the like. Such components can be connected together in a network to define a fluid flow path. Some fluid systems are open systems, meaning that the fluid flows through the network once and then exits the network. Other fluid systems are closed systems, meaning that the fluid recirculates within the network of components. Fluids are caused to flow in the fluid system using fluid pressure differentials. In some cases, a pump is used to create a pressure differential that causes the fluid to flow within the fluid system. In other cases, a vacuum source, gravity, or a combination of such techniques can be used to create a pressure differential that causes the fluid to flow within the fluid system.

Reservoirs can be used as components of fluid systems for various purposes. In some cases, reservoirs are used for accumulation or storage of the fluid. The storage of a fluid in a reservoir can facilitate a steady outgoing flow of the fluid, despite having an unsteady incoming flow of the fluid. Reservoirs can also be used to facilitate control of the pressure of the fluid within the fluid system. Some reservoirs are completely filled with the fluid, while other reservoirs include an airspace above the level of the fluid in the reservoir.

In the case of a closed reservoir which is not open to ambient atmospheric pressure, the pressure within a reservoir may be higher or lower than the ambient air pressure on the outside of the reservoir. Such pressure differentials can be advantageous when the extent of the pressure differential is within the design parameters of the fluid system. However, in some circumstances the pressure differential between the ambient air and the interior of a reservoir can become greater than intended, and undesirable consequences can result. Such undesirable consequences may include deviating from being in a state of control of the fluid flow, excessive pressure or vacuum levels within the fluid system, damage to the reservoir or another fluid system component, and the like.

Fluid systems are often used in a medical context. Some examples of fluid systems used in the medical context include respiratory systems, anesthesia systems, infusion pump systems, blood transfusion circuits, kidney dialysis systems, extracorporeal membrane oxygenation (ECMO) systems, extracorporeal circuits for heart/lung bypass, and the like. Some such medical fluid systems include the use of medical fluid reservoirs.

As with other types of fluid reservoirs, medical fluid reservoirs may experience a pressure differential between the ambient air and the interior of the medical fluid reservoir that is greater than intended. In some cases, excessive differential pressures can result in undesirable consequences that may damage the medical fluid system or could hamper the desired fluid flow. To avoid such undesirable pressure differentials, one or more pressure relief valves have been used in fluid communication with a reservoir. One such relief valve is disclosed in U.S. Pat. No. 9,435,450, entitled "Pressure Differential Relief Valve," which is incorporated herein by reference in its entirety.

In the medical context, devices that come in contact with blood or other patient fluids must meet special requirements such as biocompatibility and sterility, for example. A single unit providing relief for both excessive negative pressure and excessive positive pressure is very desirable. High reliability for performing pressure relief is necessary, and a compact design would be beneficial for incorporating a valve into a reservoir in a convenient location while avoiding any need to increase the size of the reservoir. In addition, a low cost is highly desirable in order to enable disposability of devices (which further increases patient safety). These potentially conflicting criteria have created an ongoing need for improvement in pressure relief valves.

SUMMARY OF THE INVENTION

In some embodiments, the invention provides two-way pressure relief in a single valve device which combines a ball valve and a diaphragm valve in a shared housing. The compact design achieves low material and manufacturing costs. The valve of the invention provides reliable, robust sealing and enables any desired thresholds for both negative and positive pressure to be easily obtained with simple variations of an overall design.

In one aspect of the invention, a differential pressure relief valve for a medical reservoir comprises a housing body forming a recessed chamber with an upper opening and first and second subchambers side by side in fluid communication. The first subchamber defines a positive pressure port comprised of a first opening in a bottom surface of the housing body with a first valve seat in the first subchamber along an inner perimeter of the first opening. The second subchamber defines a negative pressure port comprised of at least one second opening in the bottom surface of the housing body with a second valve seat on the bottom surface of the housing body along an outer perimeter of the second opening. A diaphragm member is biased against the second valve seat and is configured to deflect off of the second valve seat in response to a predetermined negative pressure. A sealing ball is gravitationally biased against the first valve seat and is configured to raise off of the first valve seat in response to a predetermined positive pressure. A cover sheet is disposed at an upper surface of the housing body to partially enclose the chamber and trap the sealing ball in the first subchamber. The cover sheet includes an aperture aligned with the second subchamber providing an ambient pressure port coupling the chamber to an ambient atmosphere.

DETAILED DESCRIPTION OF PREFERRED EMBODIMENTS

Figure 1:
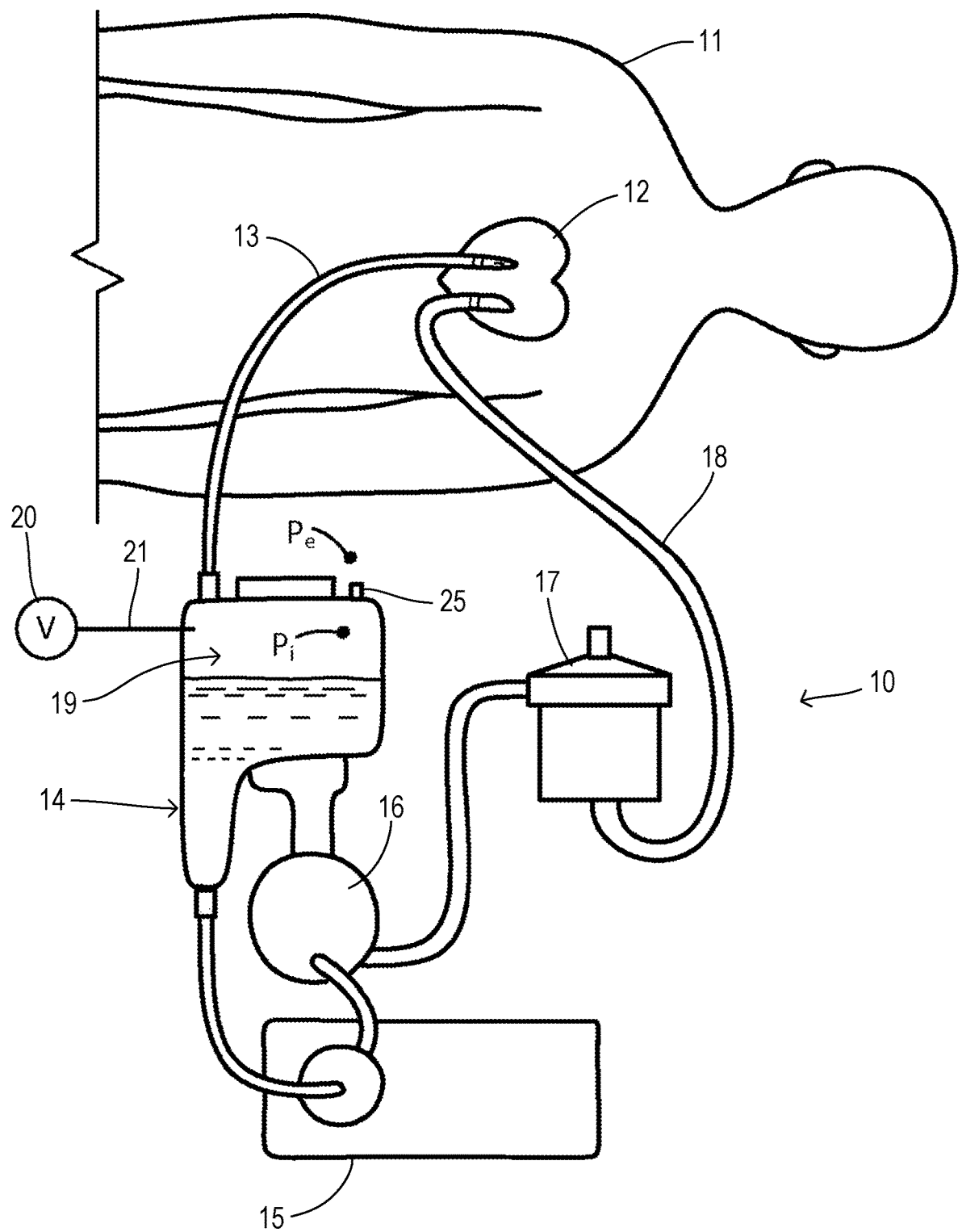
FIG. 1 is a schematic diagram of patient undergoing an example medical procedure using an extracorporeal blood flow circuit that includes a medical fluid reservoir.

Referring to FIG. 1, a patient 11 can receive a medical treatment while using a medical fluid system 10. In this illustrative example, patient 11 is undergoing a heart bypass procedure using an extracorporeal blood flow circuit 10 connected to patient 11 at the patient's heart 12. Blood from patient 11 is extracted at or near heart 12, the blood is circulated through circuit 10, and then the blood is returned to the patient's heart 12.

Extracorporeal blood flow circuit 10 includes, at least, a venous tube 13, a blood reservoir 14, a pump 15, an oxygenator 16, an arterial filter 17, and an arterial tube 18. Venous tube 13 is in physical contact with heart 12 and in fluid communication with the venous side of the circulatory system of patient 11. Venous tube 13 is also in fluid communication with an inlet to reservoir 14. An outlet from reservoir 14 is connected by tubing to an inlet of pump 15. The outlet of pump 15 is connected to tubing to an inlet of oxygenator 16. The outlet of oxygenator 16 is connected by tubing to an inlet of arterial filter 17. An outlet of arterial filter 17 is connected to arterial tube 18. Arterial tube 18 is in physical contact with heart 12 and in fluid communication with the arterial side of the circulatory system of patient 11.

Briefly, extracorporeal blood flow circuit 10 operates by removing venous blood from patient 11 via venous tube 13. Blood from venous tube 13 is deposited in reservoir 14. At least some amount of blood is intended to be maintained in reservoir 14 at all times during the medical procedure. Blood from reservoir 14 is drawn from reservoir 14 by pump 15. The pressure generated by pump 15 propels the blood through oxygenator 16. In oxygenator 16 the venous blood is enriched with oxygen. The oxygen-rich arterial blood exits oxygenator 16, travels through arterial filter 17, and is injected into the patient's heart 12 by arterial tube 18.

The flow of blood through the extracorporeal blood flow circuit 10 is essentially continuous while the medical procedure is taking place. Within that overall context, an accumulation of blood exists in reservoir 14 during the procedure. The accumulation of blood within reservoir 14 serves multiple purposes. In one aspect, the accumulation of blood in reservoir 14 provides a buffer amount to help ensure a continuous flow of oxygenated blood to patient 11, even in the event that blood flow to reservoir 14 is interrupted. In another aspect, reservoir 14 allows the venous blood to deaerate. The deaeration of the venous blood takes place by allowing air bubbles in the blood to escape the blood and flow into the air. For at least that reason, an airspace 19 is maintained in reservoir 14.

As described above, the venous blood flows (drains) from heart 12 to reservoir 14. In some implementations, the venous blood drainage from heart 12 to reservoir 14 occurs primarily as a result of gravity. In such gravity drainage implementations, reservoir 14 is positioned at a lower elevation than heart 12. In result, the blood naturally flows 'downhill' from heart 12 to reservoir 14. In some implementations, a vacuum is drawn in the airspace 19 of reservoir 14 to assist with the drainage from heart 12 to reservoir 14. This technique is known as vacuum assisted venous drainage (VAVD).

During VAVD procedures, the venous drainage is assisted by placing reservoir 14 under a negative pressure (vacuum) in relation to the ambient pressure. For example, in some implementations a negative pressure is achieved within airspace 19 using a vacuum source 20 that is connected to reservoir 14 via a vacuum line 21. Vacuum source 20 is used to reduce an air pressure $P_i$ that is in interior airspace 19 of reservoir 14 to less than an air pressure $P_e$ at an ambient location that is externally adjacent to reservoir 14 (i.e., at atmospheric ambient pressure). To maintain an effective level of vacuum in airspace 19 when using VAVD, reservoir 14 is sealed in an essentially airtight manner. Consequently, an air pressure differential may exist between $P_i$ and $P_e$. Under normal operating conditions, the pressure differential between $P_i$ and $P_e$ (e.g., where $P_i<P_e$) is beneficial for assisting with the drainage of blood from heart 12 to reservoir 14.

In some scenarios, however, the pressure differential between $P_i$ and $P_e$ can become abnormal, and undesirable consequences can result. For example, in the event that vacuum line 21 becomes blocked or kinked, vacuum withdrawal of air from reservoir 14 might stop, and reservoir 14 (being sealed airtight) could build up a positive pressure at $P_i$ in relation to $P_e$. In that case, it is possible that pressurized air from airspace 19 can be forced from reservoir 14, through venous tube 13, and into heart 12 of patient 11. In another example, an excess of vacuum in reservoir 14 (too high of a pressure differential between $P_i$ and $P_e$) can result if there is a failure of a regulator of vacuum source 20, or if an incorrect set point is used for vacuum source 12. In such a case, the excess vacuum in airspace 19 of reservoir 14 can pull air across the membrane of oxygenator 16, causing air to be potentially sent to patient 11 via arterial tube 18. In some cases, excess negative pressure can also damage the blood cells. For these and other such reasons, the pressure differential between $P_i$ and $P_e$ can be beneficial when controlled within a desirable range of pressure, but can be detrimental when outside (above or below) the desirable range of pressure. Hence, a pressure differential relief device 25, that remedies both an excessive vacuum situation and an overpressure situation, can be advantageously used in conjunction with the reservoir 14. The benefits of such a pressure differential relief device can also be realized in the context of fluid circuits other than the example extracorporeal blood flow circuit 10, including in other medical applications.

Figure 2:
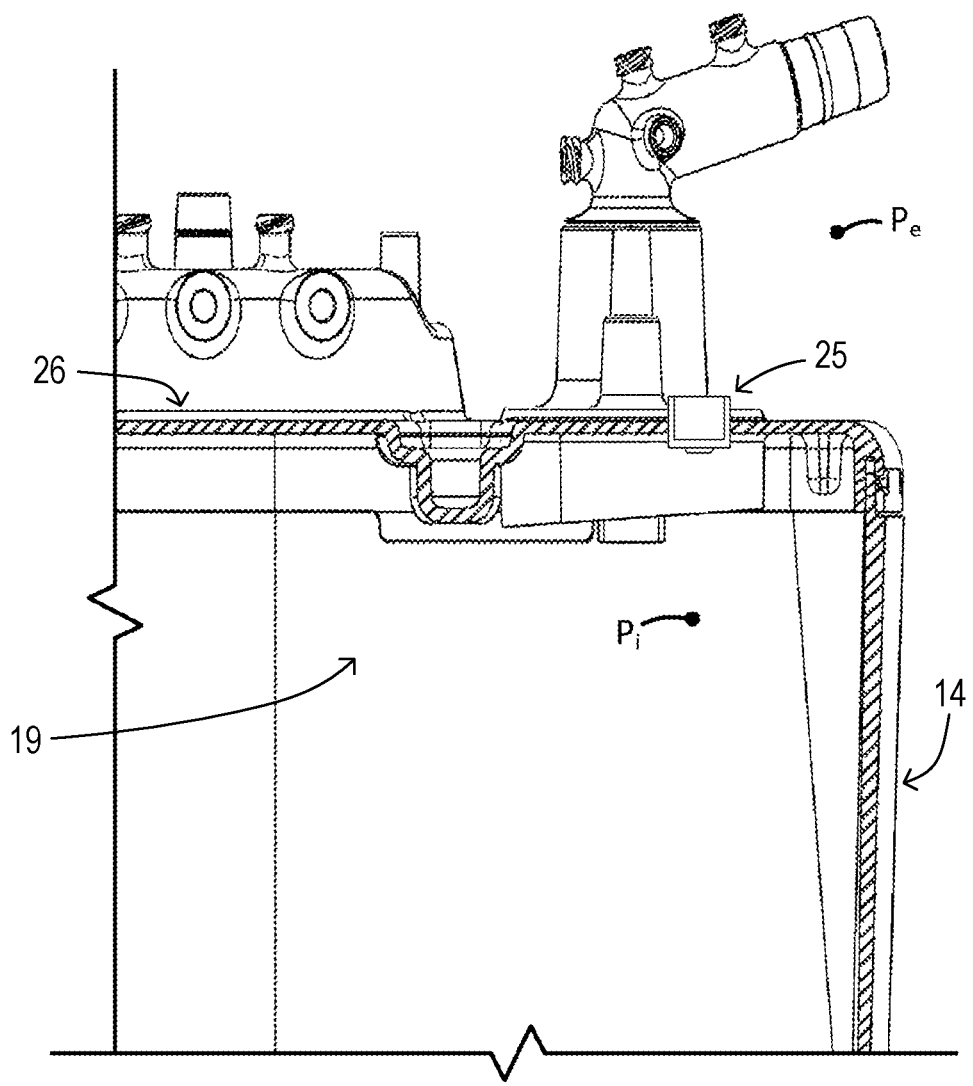
FIG. 2 is a partial cross-sectional view of an example medical fluid reservoir that includes a pressure differential relief valve in accordance with some embodiments provided herein.

As shown in FIG. 2, reservoir 14 can be formed as a plastic shell which includes a lid 26 for mounting pressure differential relief valve 25 to facilitate equalization of both positive and negative pressure differentials between $P_i$ and $P_e$. Lid 25 may also incorporate a connector for a venous tube. Valve 25 may be installed in an aperture through lid 26 so that one side of valve 25 is exposed to interior airspace 19 inside of the reservoir shell and the other side of valve 25 is exposed to an exterior space outside of the reservoir shell that has an ambient atmospheric pressure. Valve 25 may be coupled with lid 26 of the reservoir shell in a variety of ways including, but not limited to, using a snap fit, an adhesive bond, a weld, a threaded connection, a compression fit, a bayonet connection, a luer fitting, and the like. In some cases, a seal or a gasket, such as one or more O-rings, may be included. In some embodiments, valve 25 or portions of valve 25 may be integrally molded with portions of reservoir 14. In alternative embodiments, valve 25 may be engaged with reservoir 14 using a tube, a fitting, a coupling, and the like.

Figure 3:
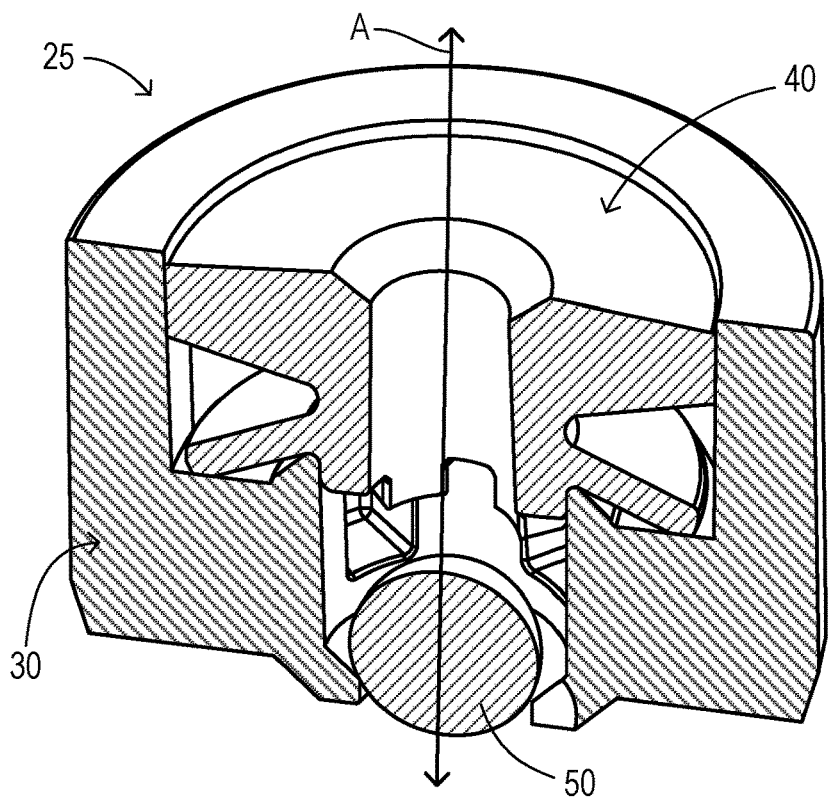
FIG. 3 is a center, vertical cross-sectional view of a relief valve according to a first embodiment.

A first embodiment of two-way pressure relief valve 25 is shown in greater detail in FIGS. 3-11. The cross section of FIG. 3 shows a main body 30, a sealing disk 40, and a sealing ball 50 of valve 25, wherein a ball valve for positive pressure relief and a diaphragm valve for negative pressure relief are both in a closed state.

A main body 30, which is adapted to mount into a wall of the reservoir, is formed of a rigid biocompatible material (e.g., a molded thermoplastic). Main body 30 is generally cup-shaped with a central chamber 31. Chamber 31 is tiered, so that a flat ledge forms an outer radial seat 32 extending annularly around a center axis A of valve 25. Preferably, outer radial seat 32 is a flat annular surface oriented perpendicular to center axis A, but can be frustoconical or other shapes that can form a controllable seal with sealing disk 40. An upper portion of chamber 31 receives sealing disk 40 and a lower portion of chamber 31 forms a positive-pressure port at center axis A with an inner radial seat 33 around a central opening that receives sealing ball 50.

Figure 4:
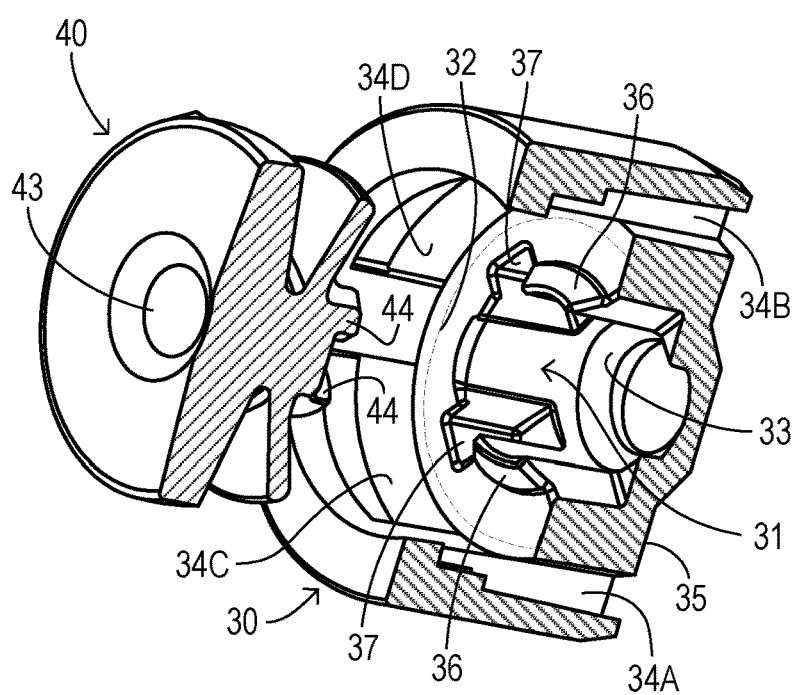
FIG. 4 is an off-center cross-sectional view of a main body and a sealing disk of the relief valve of FIG. 3.
Figure 5:
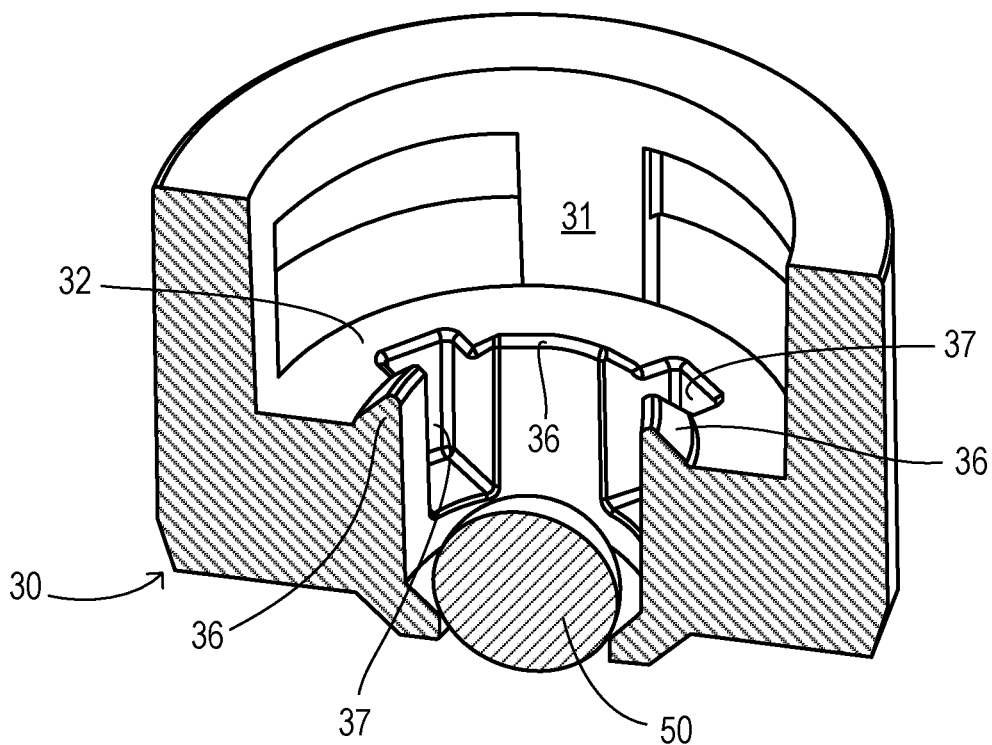
FIG. 5 a vertical cross-sectional view of the main body and a sealing ball of the relief valve of FIG. 3.
Figure 6:
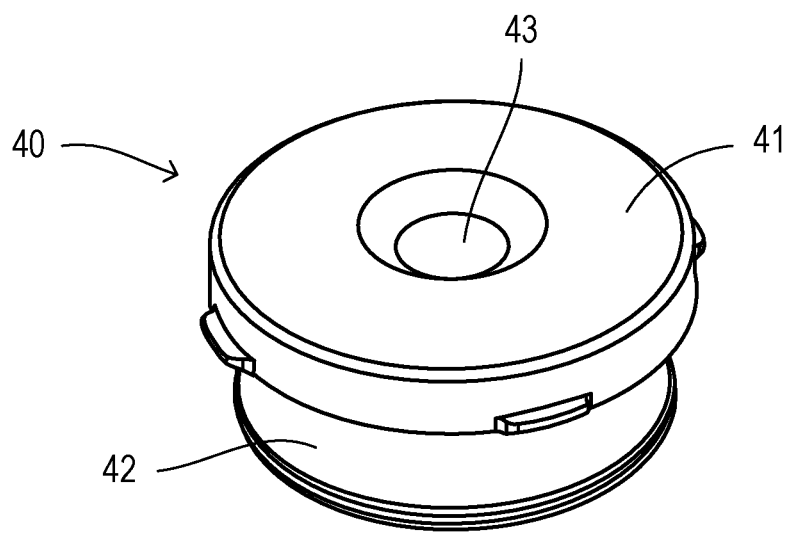
FIGS. 6 and 7 are perspective views of the sealing disk of FIG. 3.

Main body 30 has one or more internal passages spanning outer radial seat 32 in order to provide a negative-pressure port. As shown in FIG. 4, main body 30 has internal passages 34A, 34B, 34C, and 34D extending axially from a bottom surface 35 (providing the negative pressure port) to openings in an inner cylindrical surface of main body 30 above outer radial seat 32. Passages 34A, 34B, 34C, and 34D are annularly spaced around the periphery of outer radial seat 32. By spanning outer radial seat 32, the negative pressure port can be fluidically coupled to ambient external air by opening of the diaphragm valve as described below. Resulting flowpaths 60 and 61 provide negative pressure relief.

Sealing disk 40 retained in central chamber 31 comprises an anchor body 41 and a flexible diaphragm 42. Disk 40 is preferably formed as a solid block of a resilient material, such as a biocompatible silicon rubber. In cross section, anchor body 41 and diaphragm 42 have a butterfly shape, wherein diaphragm 42 is bendable toward and away from anchor body 41. Preferably, diaphragm 42 is shaped as an annular flange extending from anchor body 41 with a frustoconical shape. Anchor body 41 is fixed (e.g., glued, press-fit, or snapped) to main body 30 within the upper portion of central chamber 31 such that diaphragm 42 is biased against outer radial seat 32. Anchor body 41 defines an axial passage 43 coupling central chamber 31 to the external air at ambient pressure (e.g., atmospheric pressure outside the reservoir).

Main body 30 further defines axial wedges 36 alternating with adjacent axial grooves 37. Wedges 36 extend upward to bear against sealing disk 40 at the base of diaphragm 42. Grooves 37 between wedges 36 fluidically couple an ambient-pressure side (i.e., lower surface) of diaphragm 42 to ambient pressure via axial passage 43 of sealing disk 40. A reservoir-pressure side (i.e., upper surface) of diaphragm 42 is fluidically coupled to the interior airspace (i.e., internal pressure $P_i$) by passages 34A-34D.

Figure 7:
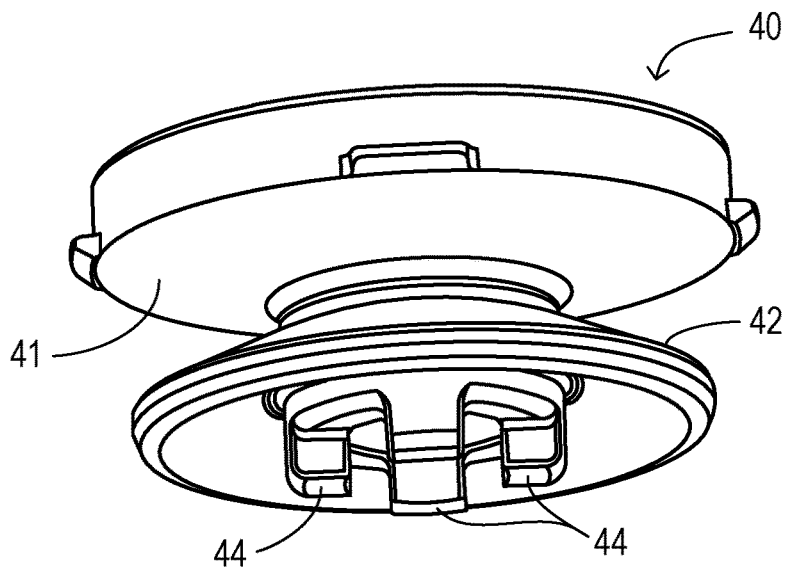
Figure 8:
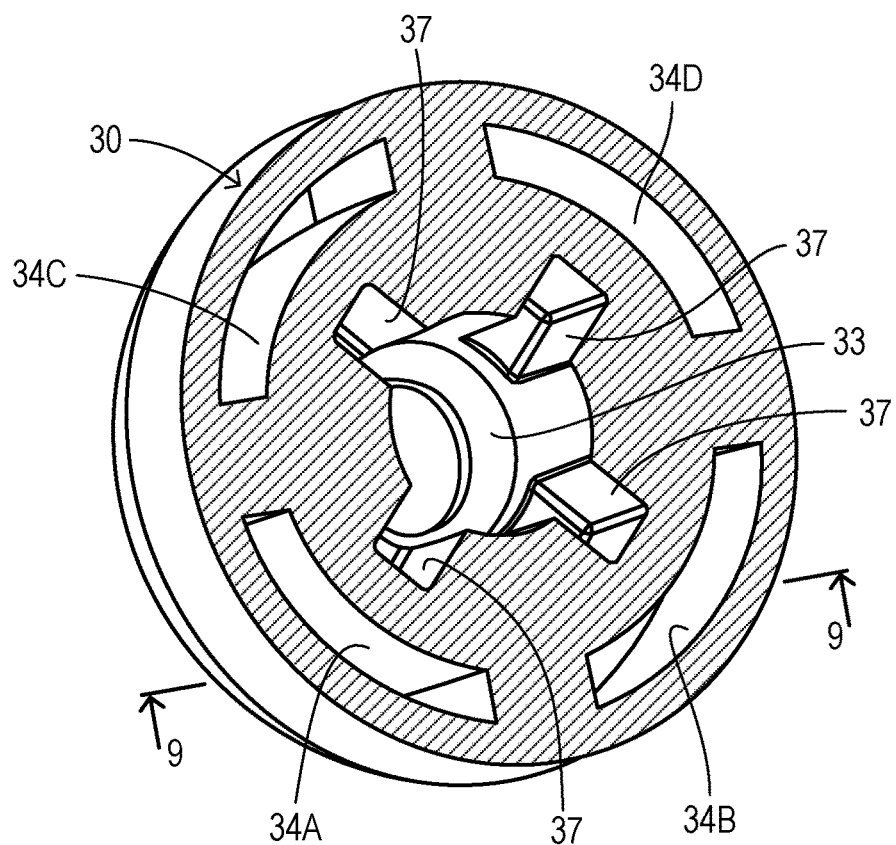
FIG. 8 is a horizontal, cross-sectional view of the main body of the relief valve of FIG. 3.
Figure 9:
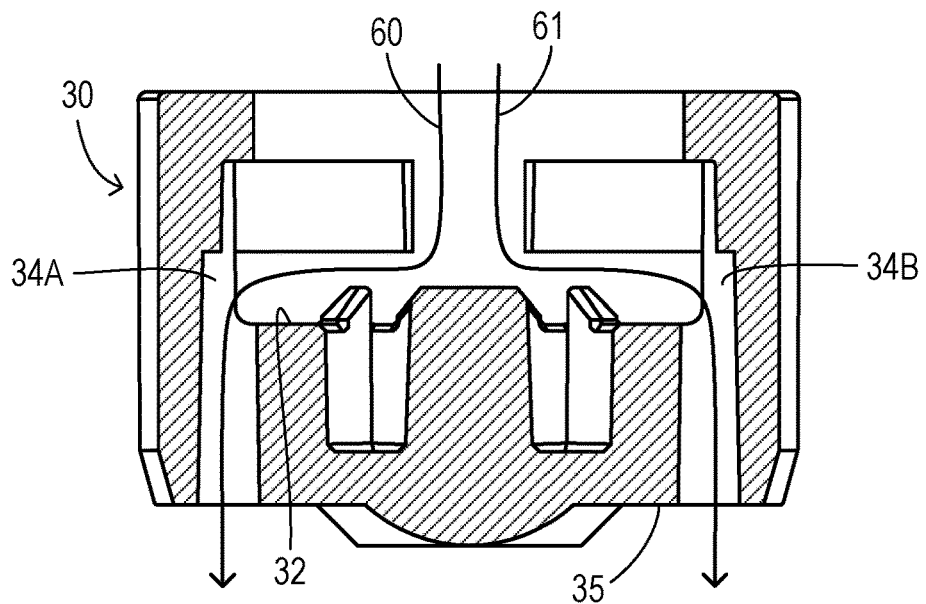
FIG. 9 is a vertical, cross-sectional view of the main body of FIG. 3 taken along line 9-9 of FIG. 8, indicating gas flowpaths for negative pressure relief.

Sealing ball 50 may be comprised of a resilient material (such as nylon). In the embodiment of FIGS. 3-11, ball 50 is biased against inner radial seat 33 by gravity (i.e., by the weight of ball 50). For achieving a good seal, inner radial seat 33 may have a frustoconical surface. As shown in FIGS. 4 and 7, sealing disk 40 preferably includes a plurality of axial protrusions 44 which are annularly spaced to receive ball 50 when it moves to an upper (full open) position. Protrusions 44 limit the lifting of sealing ball 50 to maintain open spaces between protrusions 44 which prevents blocking of axial passage 43 by ball 50. With ball 50 lifted off of inner radial seat 33, a gas flowpath for positive pressure relief is provided through the central opening of main body 30 and axial passage 43 of sealing disk 40.

Figure 10:
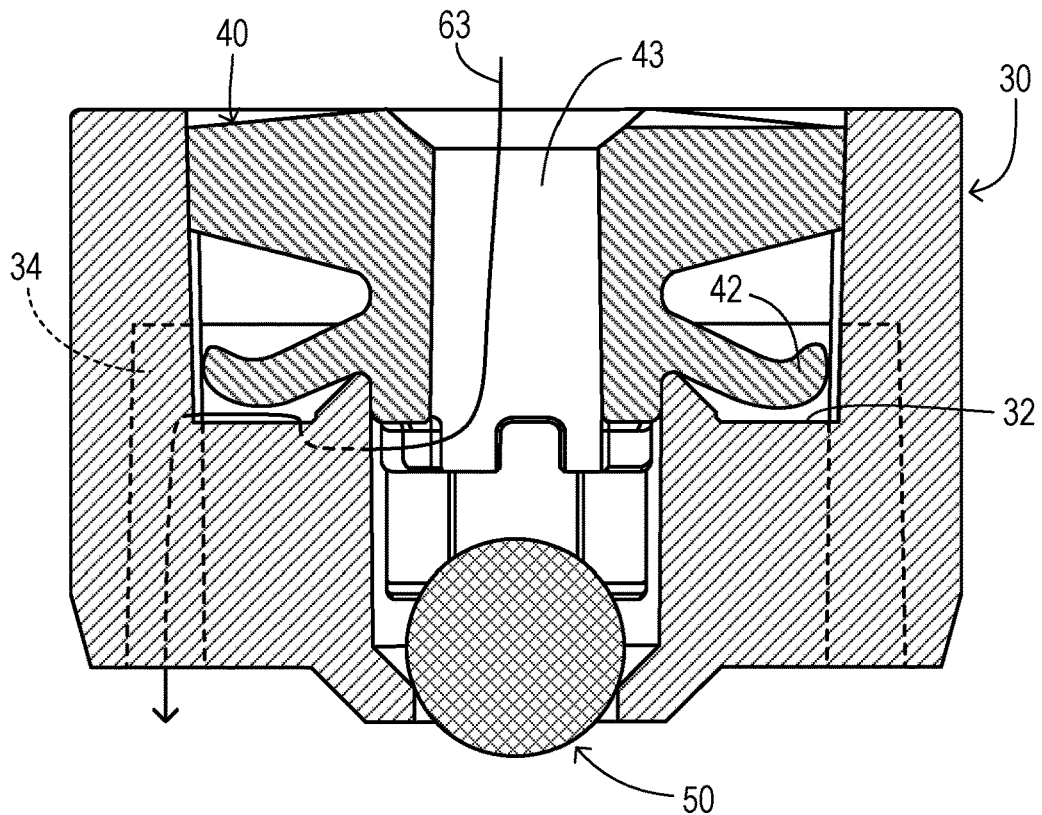
FIG. 10 is a vertical, cross-sectional view of the relief valve of FIG. 3 indicating gas flowpaths for negative pressure relief.

When a pressure differential across valve 25 is low or below selected thresholds, ball 50 and diaphragm 42 are seated against valve seats 32 and 33. As shown in FIG. 10, when the pressure inside the reservoir ($P_i$) is below the external ambient pressure ($P_e$) by a negative-pressure threshold, then diaphragm 42 is lifted off outer radial seat 32 to intake a gas from the atmosphere into the reservoir through axial passage 43, internal passages 34, and the negative-pressure port where passages 34 meet surface 35 (e.g., along flowpath 63). The negative-pressure threshold can be determined according to a shape and thickness of diaphragm 42, its constituent material properties, and an amount of bias deflection determined by its placement relative to outer radial seat 32.

Figure 11:
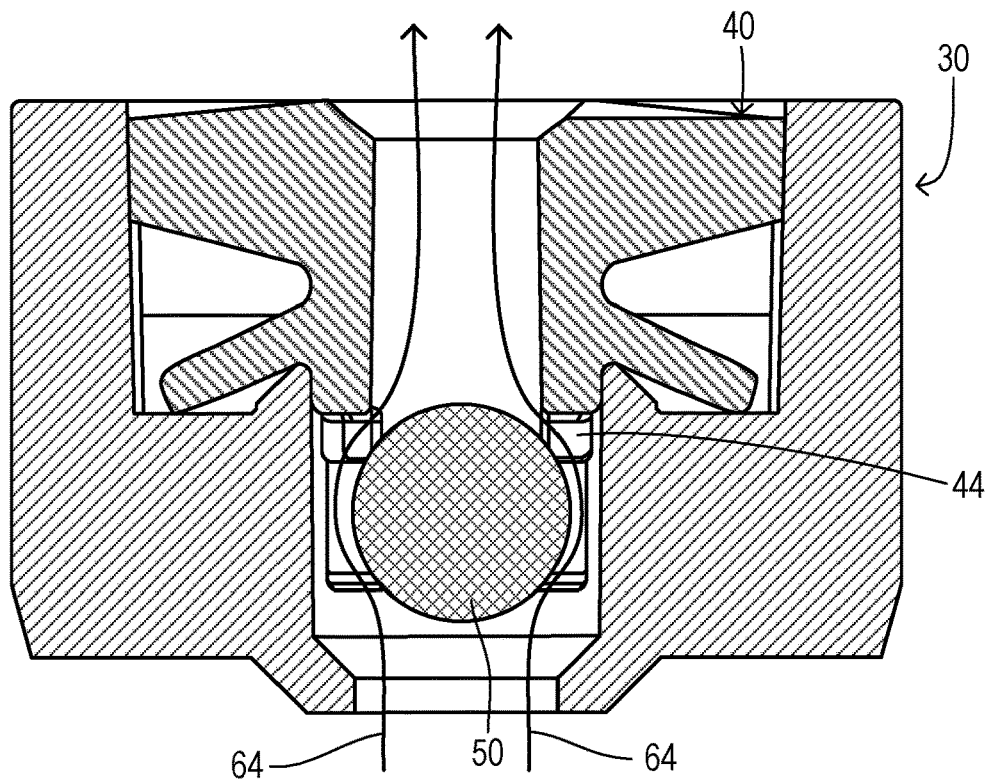
FIG. 11 is a vertical, cross-sectional view of the relief valve of FIG. 3 indicating gas flowpaths for positive pressure relief.

As shown in FIG. 11, when a pressure inside the reservoir ($P_i$) exceeds the ambient pressure by a positive-pressure threshold, then sealing ball 50 is lifted off inner radial seat 33 to exhaust a gas from the reservoir through the positive-pressure port (e.g., center hole) and axial passage 43 to the external airspace (i.e., atmosphere) along a flowpath 64. The positive-pressure threshold can be determined according to a size (e.g., weight) and constituent material properties of ball 50.

Figure 12:
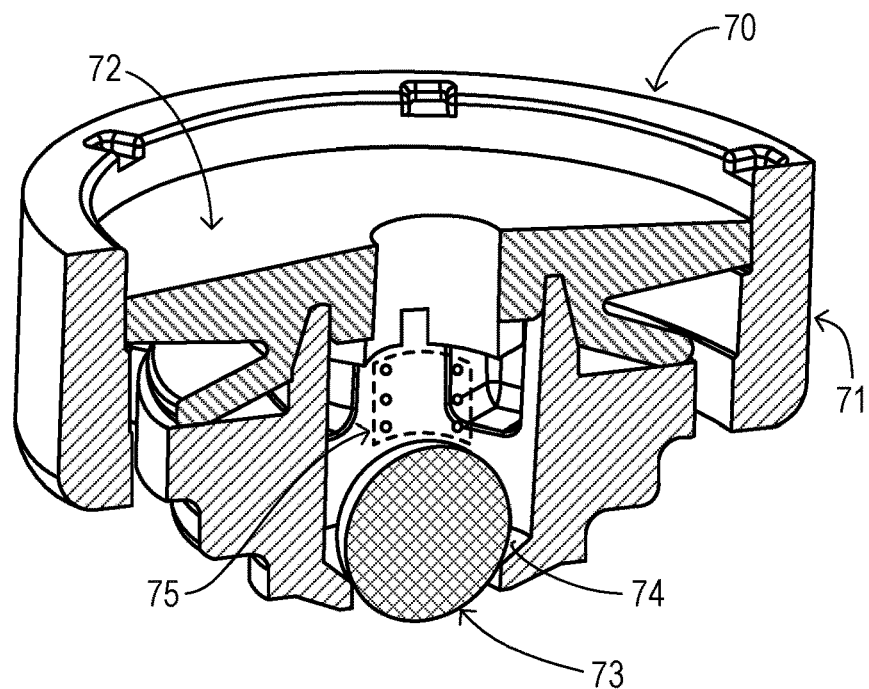
FIG. 12 is a vertical, cross-sectional view of a relief valve according to another embodiment of the invention.

FIG. 12 show an alternative embodiment of a two-way pressure relief valve 70 having slightly different dimensions, resulting in different pressure thresholds, for example. A main body 71 receives a sealing disk 72 and a sealing ball 73. In addition to the weight of ball 73 biasing is against a valve seat 74, a compressible body 75 is disposed between ball 73 and sealing disk 72. Compressible body 75 is configured to bias sealing ball 73 against valve seat 74 according to a force selected to provide the desired positive-pressure threshold. Compressible body 75 can be comprised of a toroidal spring, for example.

Figure 13:
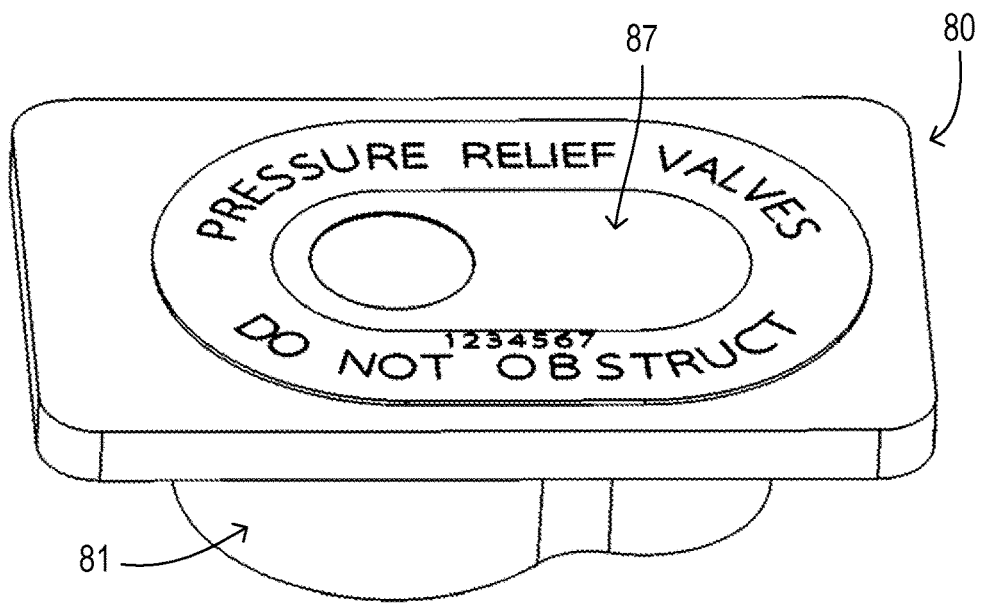
FIG. 13 is a top, perspective view of a pressure relief valve using a retaining label according to a further embodiment.
Figure 14:
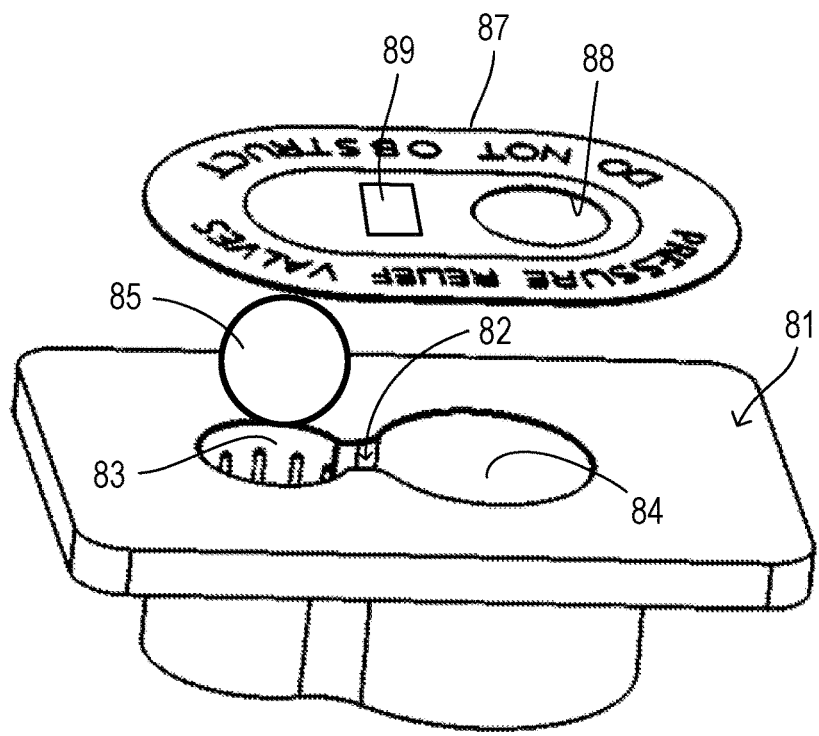
FIG. 14 is an exploded view of the relief valve of FIG. 13.
Figure 15:
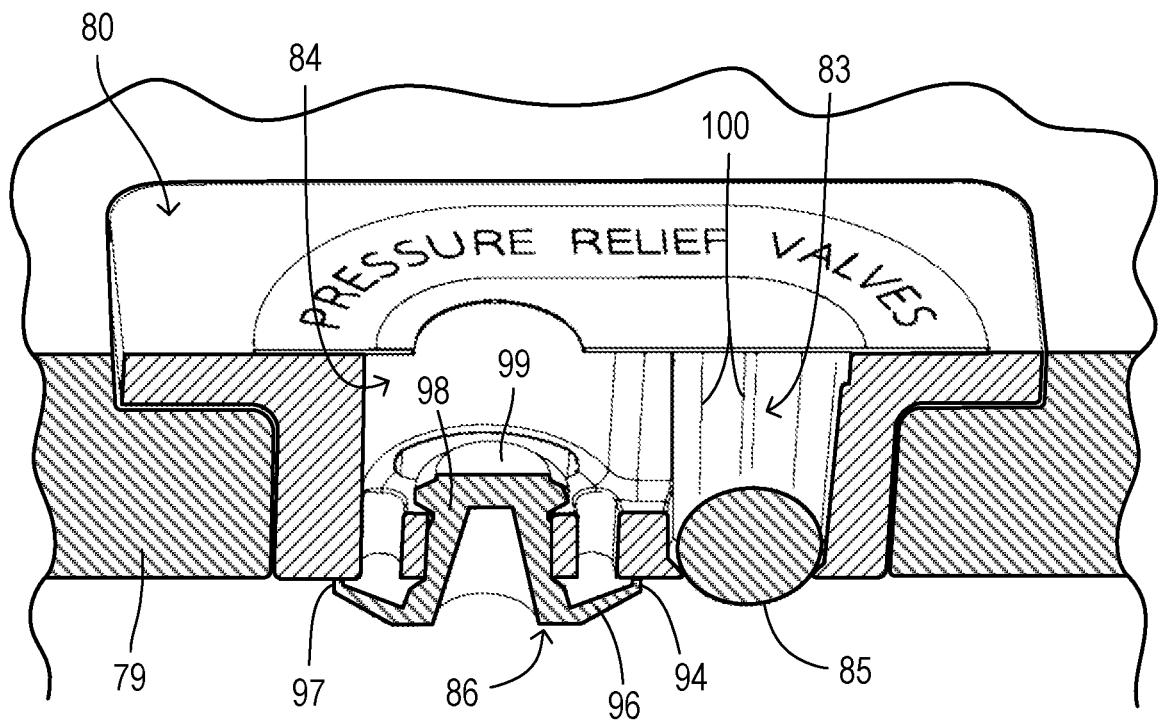
FIG. 15 is a vertical cross-sectional view of the relief valve of FIG. 13.

FIGS. 13-21 show another embodiment of a combined positive/negative pressure relief valve 80 configured to fit into an opening in an upper wall (e.g. lid) of a reservoir. For example, FIG. 15 shows valve 80 affixed to a reservoir wall 79 within a corresponding opening in a sealed manner so that an interior of the reservoir is isolated from external atmosphere except when a pressure in the reservoir goes outside a pressure range from a negative pressure threshold to a positive pressure threshold. Valve 80 is particularly simple to manufacture and assemble, and integrates labeling/marking functions into a structure that also provides an ambient pressure port and entraps a valve component in an inner chamber of the valve.

As shown in FIGS. 13 and 14, valve 80 has a housing body 81 forming a cup-like structure having a recessed chamber 82 with an upper opening. Chamber 82 has a first subchamber 83 and a second subchamber 84 arranged side by side and in direct fluid communication with each other. First subchamber 83 retains a sealing ball 85 to implement a positive pressure relief section (e.g., which opens when a positive pressure in the reservoir exceeds a positive pressure threshold). Second subchamber 84 retains a diaphragm member 88 to implement a negative pressure relief section (e.g., which opens when a negative pressure in the reservoir falls below a negative pressure threshold). A cover sheet 87 is affixed to an upper surface of housing body 81 to partially enclose chamber 82 and to trap sealing ball 85 in first subchamber 83. Cover sheet 87 includes an aperture 88 aligned with second subchamber 84 providing an ambient pressure port which couples chamber 82 to ambient atmosphere and pressure.

Figure 16:
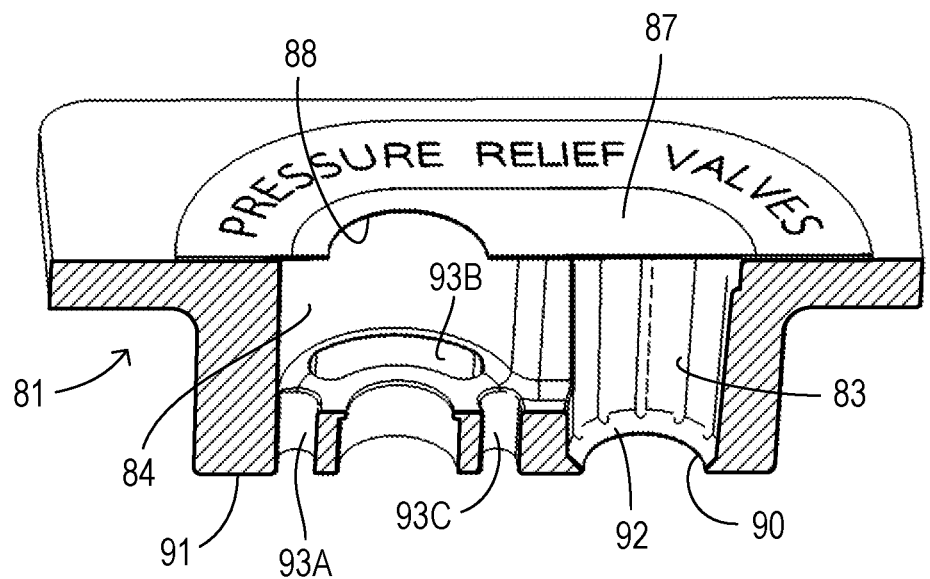
FIG. 16 is a vertical cross-sectional view of the relief valve of FIG. 13 with a sealing ball and a diaphragm member being removed.
Figure 17:
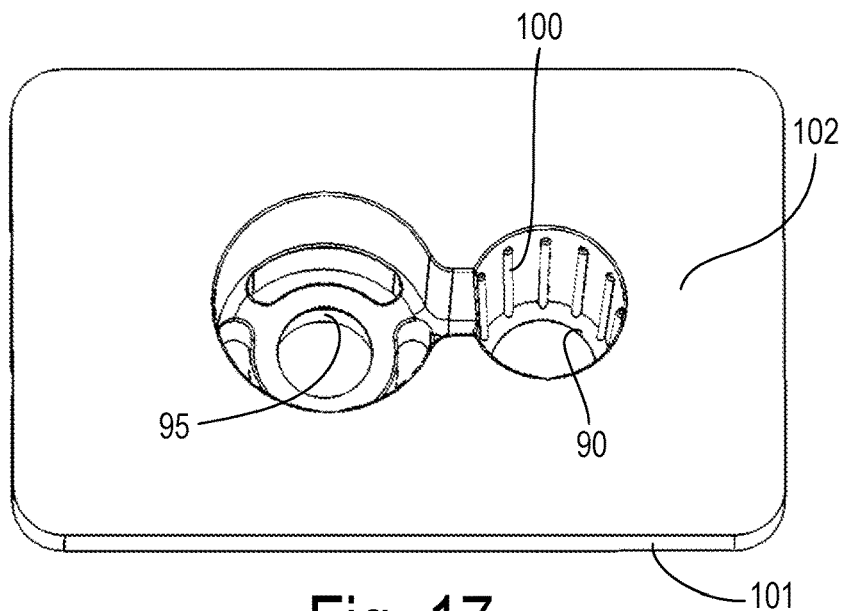
FIG. 17 is a top view of a housing body of the relief valve of FIG. 13.
Figure 18:
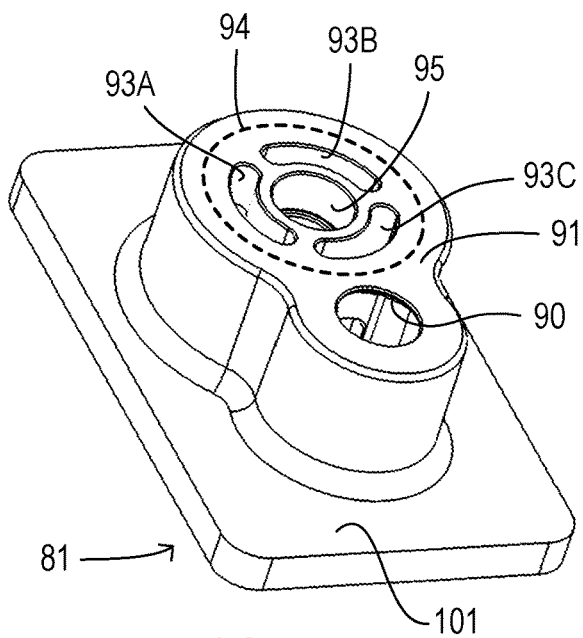
FIG. 18 is a bottom, perspective view of the housing body of the relief valve of FIG. 13.

FIGS. 15 and 16 show the normal (i.e., sealing) positions of sealing ball 85 and diaphragm member 86. First subchamber 83 defines a positive pressure port comprised of a first opening 90 in a bottom surface 91 of housing body 81. A sloped rim 92 provides a first valve seat along an inner perimeter of first opening 90 for receiving sealing ball 85. Second subchamber 84 defines a negative pressure port comprised of second openings 93A, 93B, and 93C in bottom surface 91. As seen in FIG. 18, a second valve seat 94 on bottom surface 91 of housing body 81 extends along an outer perimeter of second openings 93A, 93B, and 93C. Openings 93A-93C are preferably formed as separate arcuate slots along a predetermined circumference which is disposed radially inwardly from second valve seat 94.

Figure 20:
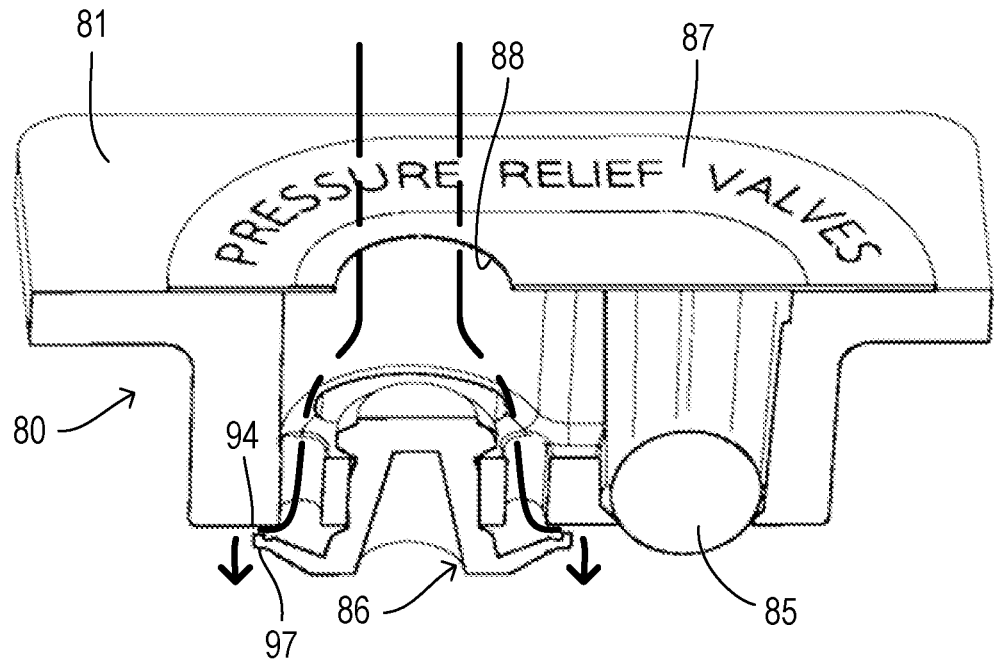
FIG. 20 is a cross-sectional view showing the relief valve of FIG. 13 is a state of relieving a negative pressure in the reservoir.

A mounting hole 95 extends through bottom surface 91 at a radial center of the circumferential path of second openings 93A-93C. Diaphragm member 86 is an umbrella-type flap valve having a sloping central apron 96 with an outer edge 97 which is biased against second valve seat 94. Apron 96 is supported by a central shaft section 98 which is retained in mounting hole 95 with an enlarged hub 99 disposed inside subchamber 84. Diaphragm member 86 is made of a flexible, resilient material such as silicone polymer and shaft section 98 is hollow so that hub 99 and shaft section 98 can be pulled through mounting hole 95 for installation onto housing body 81. As a result of the dimensions of shaft section 98 and apron 96 and of the flexibility of apron 96, a preload force biases edge 97 against second valve seat 94. In response to a pressure in the reservoir that is below a predetermined negative pressure threshold, the force from ambient pressure acting through openings 93A-93C overcomes the preload force so that edge 97 deflects off of second valve seat 94 (as shown in FIG. 20).

Figure 21:
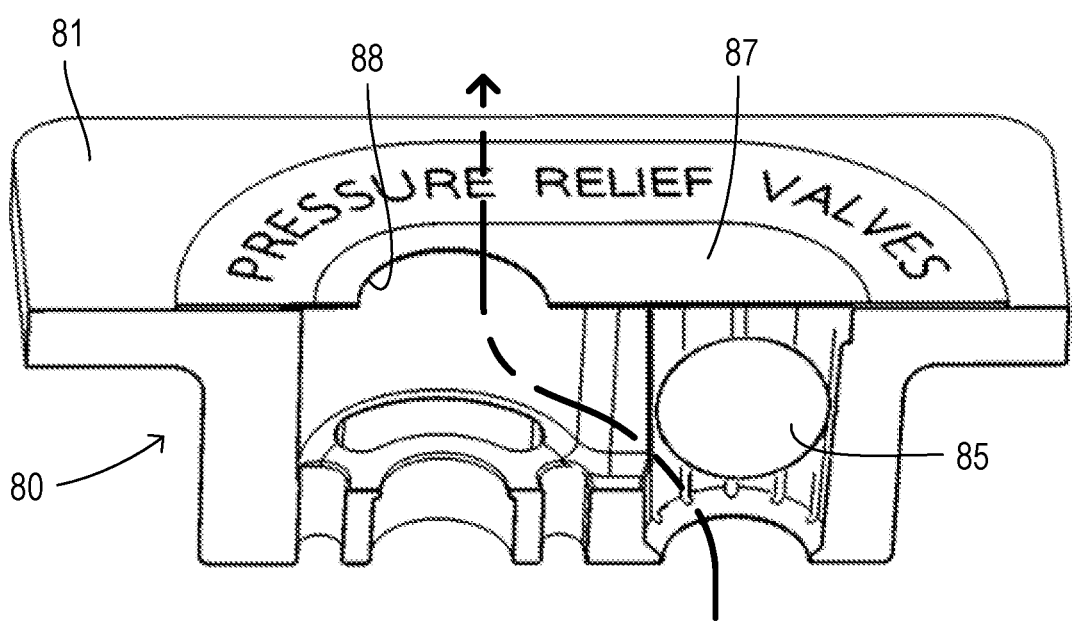
FIG. 21 is a cross-sectional view showing the relief valve of FIG. 13 is a state of relieving a positive pressure in the reservoir.

Subchamber 83 defines a generally cylindrical region for receiving sealing ball 85. A plurality of ribs 100 along the sides of subchamber 83 maintain an open central space slightly larger than the diameter of sealing ball 85 to allow freedom of up and down motion of ball 85. Radial spaces between adjacent ribs 100 ensure adequate airflow across the valve. Sealing ball 85 is gravitationally biased against first valve seat 92. A compliant material such as nylon is used to form sealing ball 85 in order to obtain a good seal across first valve seat 92. Preferably, first valve seat 92 may be circular and sealing ball 85 may be spherical. The weight and surface area of sealing ball 85 are configured such that in response to a pressure in the reservoir that exceeds a predetermined positive pressure threshold, then sealing ball 85 raises off of first valve seat 92 to relieve the pressure. An airflow path for positive pressure relief is shown in FIG. 21.

Figure 19:
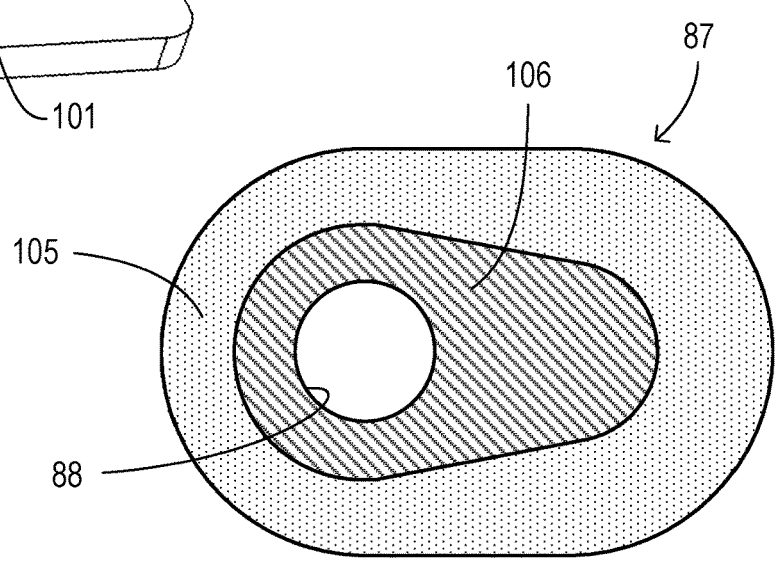
FIG. 19 is a bottom view of the cover sheet.

In a preferred embodiment, cover sheet 87 is comprised of a flexible label having multiple purposes of providing retention of sealing ball 85, providing an opening for an ambient pressure port having a desired size and location, and providing a surface for various textual and/or symbolic content such as a warning to avoid obstruction of the pressure relief opening, a product identification, a serial number, a QR code, or the like. FIG. 14 shows a region 89 on sheet 87 where a bar code or QR code can be printed. A QR code can be used for tracking a device during production, and the represented serial number provides a unique identifier after a product is shipped, for example. Labelling with this information would normally be required, and an improved manufacturing process providing a more compact unit and less overall costs can be achieved. Housing body 81 has a top plate 101 with an upper surface 102 that abuts the upper opening of chamber 82. Although plate 101 is shown with a generally rectangular shape, upper surface 102 need not be any larger than necessary to provide enough area for attaching label 87. A smaller size (such as an oval matching the size of label 87) is sufficient. The size and shape only needs to match a mounting recess in the reservoir lid. In a most preferred embodiment, housing body 81 is directly formed as an integral part of the reservoir lid. For example, chamber 82 can be formed as a recess into a top surface of the lid during injection molding of the lid. Chamber 82 may have a generally figure-8-shaped profile with a short, open channel (i.e., vent gate) providing fluid communication between subchambers 83 and 84. Flexible label 87 may have a generally oblong or oval shape larger than the upper opening of chamber 82, and an outer radial band of label 87 may be affixed to upper surface 102. FIG. 19 shows a bottom side of label 87 which includes an adhesive layer 105 at the outer radial band. An adhesive-free region 106 is provided in alignment with the sealing ball (to avoid sticking of the ball). In a preferred embodiment, flexible label 87 is comprised of a clear plastic film having a composition adapted to retain ink as printed symbols on the outer side opposite from the adhesive side.

Housing body 81 may preferably be comprised of a unitary molding, which may be injection molded using a polycarbonate material. In another embodiment, the housing body could be molded as two or more sections (e.g., split in half symmetrically similar to the view of FIG. 15). The cover sheet could be incorporated into one or both of the housing body sections such that the two halves could be assembled/bonded after inserting a sealing ball and umbrella valve. Alternatively, the housing body could be split horizontally such that a lower portion of the housing body which includes the valve seats for the two valves could be split from an upper portion incorporating the cover sheet as a separate part. Again, these parts could then be bonded after inserting a sealing ball and umbrella valve to form a positive/negative pressure relief valve.

The foregoing invention combines both positive pressure relief (via a ball valve) and negative pressure relief (via an umbrella valve) in a shared structure with a common external vent hole and an internal vent gate between the positive/negative relief valves. Retention of a sealing ball and labelling with printed symbols can be achieved by a single cover sheet.

What is claimed is:

1. A differential pressure relief valve for a medical reservoir, comprising:
   a housing body forming a recessed chamber with an upper opening and first and second subchambers side by side in fluid communication, wherein the first subchamber defines a positive pressure port comprised of a first opening in a bottom surface of the housing body with a first valve seat in the first subchamber along an inner perimeter of the first opening, and wherein the second subchamber defines a negative pressure port comprised of at least one second opening in the bottom surface of the housing body with a second valve seat on the bottom surface of the housing body along an outer perimeter of the second opening;
   a diaphragm member biased against the second valve seat and configured to deflect off of the second valve seat in response to a predetermined negative pressure;
   a sealing ball gravitationally biased against the first valve seat and configured to raise off of the first valve seat in response to a predetermined positive pressure; and
   a cover sheet disposed at an upper surface of the housing body to partially enclose the chamber and trap the sealing ball in the first subchamber, wherein the cover sheet includes an aperture aligned with the second subchamber providing an ambient pressure port coupling the chamber to an ambient atmosphere.

2. The valve of claim 1 wherein the housing body is a unitary molded body with a lid of the reservoir.

3. The valve of claim 2 wherein the housing is comprised of polycarbonate.

4. The valve of claim 1 wherein the cover sheet is comprised of a flexible label, wherein the housing body has an upper surface abutting the upper opening of the chamber, and wherein the flexible label is affixed by an adhesive to the upper surface of the housing body.

5. The valve of claim 4 wherein the flexible label includes an adhesive-free region in alignment with the sealing ball.

6. The valve of claim 4 wherein the flexible label is comprised of a clear plastic film adapted to retain ink as printed symbols on an outer side opposite an adhesive side.

7. The valve of claim 1 wherein the diaphragm member is comprised of an umbrella flap with a sloping central apron having an outer edge biased against the second valve seat.

8. The valve of claim 7 wherein the diaphragm member is comprised of silicone polymer.

9. The valve of claim 1 comprising a plurality of second openings formed as separate arcuate slots along a predetermined circumference which is disposed radially inwardly from the second valve seat.

10. The valve of claim 9 wherein the housing body includes a mounting hole extending through the bottom surface at a radial center of the predetermined circumference, and wherein the diaphragm member includes a central shaft which is retained by the mounting hole.

11. The valve of claim 1 wherein the first opening is circular, and wherein the sealing ball is spherical.

12. The valve of claim 1 wherein the sealing ball is comprised of nylon.

13. A medical fluid reservoir system, comprising:
   a reservoir shell, the reservoir shell defining an interior space inside of the reservoir shell that is configured to contain a medical fluid and an exterior space that is outside of the reservoir shell; and
   a differential pressure relief valve that is coupled to the reservoir shell, the differential pressure relief valve comprising:
      a housing body forming a recessed chamber with an upper opening and first and second subchambers side by side in fluid communication, wherein the first subchamber defines a positive pressure port comprised of a first opening in a bottom surface of the housing body with a first valve seat in the first subchamber along an inner perimeter of the first opening, and wherein the second subchamber defines a negative pressure port comprised of at least one second opening in the bottom surface of the housing body with a second valve seat on the bottom surface of the housing body along an outer perimeter of the second opening;
      a diaphragm member biased against the second valve seat and configured to deflect off of the second valve seat in response to a predetermined negative pressure;
      a sealing ball gravitationally biased against the first valve seat and configured to raise off of the first valve seat in response to a predetermined positive pressure; and
      a cover sheet disposed at an upper surface of the housing body to partially enclose the chamber and trap the sealing ball in the first subchamber, wherein the cover sheet includes an aperture aligned with the second subchamber providing an ambient pressure port coupling the chamber to an ambient atmosphere.

14. The system of claim 13 wherein the cover sheet is comprised of a flexible label, wherein the housing body has an upper surface abutting the upper opening of the chamber, and wherein the flexible label is affixed by an adhesive to the upper surface of the housing body.

15. The system of claim 14 wherein the flexible label includes an adhesive-free region in alignment with the sealing ball.

16. The system of claim 14 wherein the flexible label is comprised of a clear plastic film adapted to retain ink as printed symbols on an outer side opposite an adhesive side.

17. The system of claim 13 wherein the diaphragm member is comprised of an umbrella flap with a sloping central apron having an outer edge biased against the second valve seat.

18. The system of claim 13 comprising a plurality of second openings formed as separate arcuate slots along a predetermined circumference which is disposed radially inwardly from the second valve seat.

19. The system of claim 18 wherein the housing body includes a mounting hole extending through the bottom surface at a radial center of the predetermined circumference, and wherein the diaphragm member includes a central shaft which is retained by the mounting hole.

20. The system of claim 13 wherein the first opening is circular, and wherein the sealing ball is spherical.

* * * * *